(12) United States Patent
Chiu et al.

(10) Patent No.: US 7,205,444 B1
(45) Date of Patent: Apr. 17, 2007

(54) 1,1,1,3,3,3-HEXAFLUOROPROPANE PURIFICATION WITH PHOTOCHLORINATION EQUIPMENT

(75) Inventors: Yuon Chiu, Denville, NJ (US); David C. Merkel, West Seneca, NY (US); Hsuehsung Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 11/271,580

(22) Filed: Nov. 10, 2005

(51) Int. Cl.
*C07C 17/38* (2006.01)
*C07C 19/08* (2006.01)

(52) U.S. Cl. ............................. 570/178; 570/134
(58) Field of Classification Search ............ 570/134, 570/178
See application file for complete search history.

(56) References Cited

U.S. PATENT DOCUMENTS

| 5,190,626 A | 3/1993 | Yates et al. ............ 204/157.95 |
| 6,274,779 B1 | 8/2001 | Vasanth et al. ............ 438/305 |
| 6,551,469 B1 | 4/2003 | Nair et al. ............ 204/157.95 |

Primary Examiner—J. Parsa

(74) Attorney, Agent, or Firm—Colleen D. Szuch

(57) ABSTRACT

A continuous, vapor phase method for purifying a crude mixture of 1,1,1,3,3,3-hexafluoropropane and one or more unsaturated fluorocarbon compounds, the process comprising:
a) providing a photochlorinator vessel comprising
  1) a UV lamp unit comprising a UV lamp located in a transparent inner well, the transparent inner well being located within a transparent outer well, the outer well being provided with material for cooling walls of the inner and outer wells; the inner well and the outer well defining separate chambers isolated from each other; and
  2) a reaction vessel into which the UV lamp unit has been inserted;
b) introducing into the reaction vessel a gaseous mixture of $Cl_2$ and a distillation inseparable mixture of 1,1,1,3,3,3-hexafluoropropane and one or more unsaturated fluorocarbon compounds;
c) reacting, in the gaseous state and in the presence of UV light from the photochlorinator, the mixture with $Cl_2$ with the distillation inseparable mixture of 1,1,1,3,3,3-hexafluoropropane and one or more unsaturated compounds to saturate unsaturated fluorocarbons into a reacted mixture, and
d) separating a purified 1,1,1,3,3,3-hexafluoropropane product containing less than 1000 ppm, most preferably less than 100 ppm unsaturated fluorocarbons.

20 Claims, 3 Drawing Sheets

1,1,1,3,3,3-HEXAFLUOROPROPANE PURIFICATION WITH PHOTOCHLORINATION EQUIPMENT

FIELD OF THE INVENTION

This invention relates to a continuous, vapor phase process for purifying 1,1,1,3,3,3-hexafluoropropane (HFC-236fa) to a level of <1000 ppm, preferably <500 ppm, and more preferably <100 ppm, total unsaturates using a UV photochlorinator.

BACKGROUND OF THE INVENTION

Due to their stability, relatively low toxicity, compatibility with numerous substances, and low vaporization points, short chain fluorocarbons have been found to have utility or potential utility in industry for many purposes. Such short chain fluorocarbons (about 1 to about 5 carbon atoms) have, for example, been used as propellants, refrigerants, and solvents.

It has been asserted that certain fluorocarbons, especially chlorofluorocarbons, unfortunately may be hazardous to the environment, especially to the ozone layer. Further, impurities in certain fluorocarbons have been found to be troublesome. Unsaturated fluorocarbons are especially undesirable since many of them are toxic and are also often unstable. Such unstable unsaturated fluorocarbons can decompose into even more undesirable products which can be corrosive. It is therefore especially important for certain applications that fluorocarbons be essentially free (e.g. less than 100 ppm) of unsaturated species. There has therefore been a concerted effort to develop new and purer fluorocarbons which are viewed as being more environmentally friendly.

With respect to some fluorocarbons, it has been found possible to reduce the quantity of unsaturated species by chlorination, e.g., as described in U.S. Pat. Nos. 5,190,626 and 5,336,377. Unfortunately, the outcome of such a chlorination technique is not predictable from one fluorocarbon to another, especially when hydrogen is present in the fluorocarbon being purified. This is because hydrogen is frequently replaced by chlorine which reduces yield of the desired product and results in yet further impurities. In certain applications, such fluorocarbons must be especially pure, e.g., when they are used in particularly sensitive areas such as for refrigerants in air conditioners in confined areas.

It has been found that, 1,1,1,3,3,3-hexafluoropropane (HFC-236fa), can be used as a replacement for the fluorocarbon $CCl_2F_2CClF_2$ (CFC-114), used as a refrigerant. HFC-236fa has found particular use as a refrigerant in a closed environment. HFC-236fa can be prepared by numerous methods, e.g., as described in U.S. Pats. Nos. 5,395,997; 5,414,165; and World Patent Application WO96/15085-A1. 1,1,1,3,3,3-hexafluoropropane might be an excellent replacement for CFC-114, except that pure 1,1,1,3,3,3-hexafluoropropane has not been obtainable by known methods of preparation. This due to the fact that most known methods for the preparation of 1,1,1,3,3,3-hexafluoropropane result in residual impurities of other fluorocarbons. Unfortunately, some of the fluorocarbon impurities form low boiling azeotropes with 1,1,1,3,3,3-hexafluoropropane or are close boiling with 1,1,1,3,3,3-hexafluoropropane, which prevents separation by conventional distillation methods ("distillation inseparable mixtures"). Such distillation inseparable mixtures are obtained when an attempt is made to purify 1,1,1,3,3,3-hexafluoropropane by distillation from the reaction mixture in which it is made. This is especially troublesome since some of the impurities which form azeotropes or close boiling mixtures are unsaturated and cannot be tolerated to any significant extent in refrigerants in certain applications. Examples of such undesirable unsaturated fluorocarbon impurities are 1,1,1,3,3-pentafluoro-2-chloropropene obtained by the liquid phase reaction described in U.S. Pat. No. 5,395,997 and $C_3HCl_2F_3$ obtained by the vapor phase reaction described in U.S. Pat. No. 5,414,165.

It has been proposed in U.S. Pat. Nos. 5,856,595 and 6,274,779 B1 to purify HFC-236fa from distillation inseparable mixtures of 1,1,1,3,3,3-hexafluoropropane with at least one unsaturated fluorocarbon to obtain a 1,1,1,3,3,3-hexafluoropropane product of greater than 99.9 weight percent purity containing less than 100 parts per million of unsaturated fluorocarbons by a batch, liquid phase method that comprises:

a) reacting the mixture with chlorine to saturate the unsaturated fluorocarbons in a reacted mixture, b) distilling the reacted mixture to obtain a 1,1,1,3,3,3-hexafluoropropane, and c) removing residual HCl and chlorine from the 1,1,1,3,3,3-hexafluoropropane at any point in the method subsequent to reacting the mixture with chlorine to saturate the unsaturated fluorocarbon.

In the method of those patents, it is taught that the reaction of the mixture with chlorine is preferably conducted in the presence of ultraviolet light (UV). However, the patents do not disclose any specific UV photochlorination equipment suitable for use in accomplishing the objective of those patents, nor do patents disclose any photochlorination reaction equipment suitable for conducting the purification reaction in a continuous and vapor phase reaction while still being able to obtain a purified HFC-236fa product containing <100 ppm fluorocarbon unsaturates. It is highly desirable that such a continuous process be obtainable that produces HFC-236fa with <1000 ppm, preferably <500 ppm, and more preferably <100 ppm fluorocarbon unsaturates.

SUMMARY OF THE INVENTION

Figure 1:
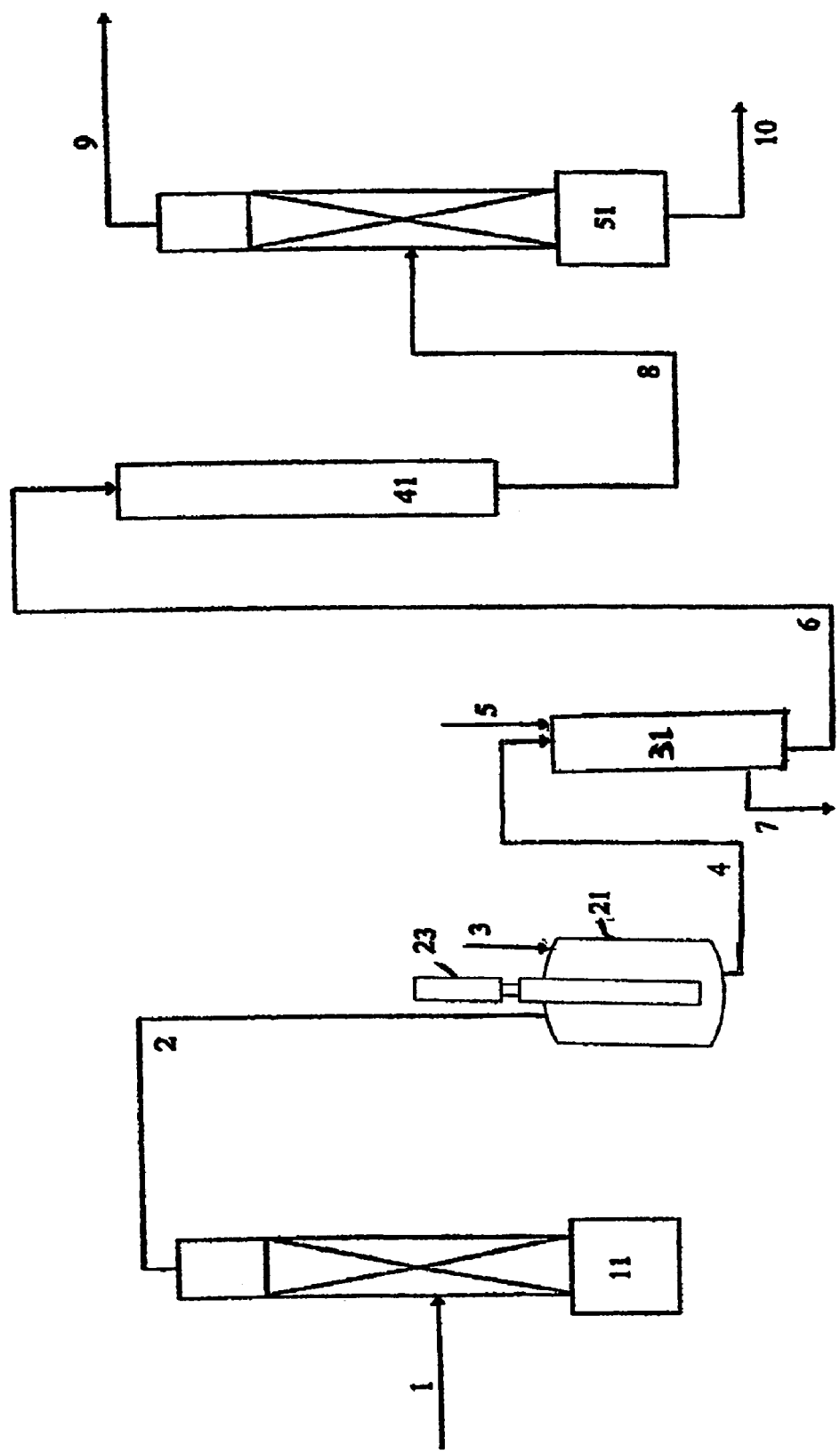
FIG. 1 is a schematic flow diagram illustrating the general method of the invention.

In accordance with the invention, a continuous, vapor phase method is provided for the purification of 1,1,1,3,3,3-hexafluoropropane from distillation inseparable mixtures of 1,1,1,3,3,3-hexafluoropropane with at least one unsaturated fluorocarbon to obtain a 1,1,1,3,3,3-hexafluoropropane product containing less than 1000 parts per million, preferably less than 500 parts per million, and more preferably less than 100 parts per million of unsaturated fluorocarbons. Such a product is such as generally to be of greater than 99.9 weight percent purity.

The invention comprises a continuous, vapor phase method for purifying a crude mixture of 1,1,1,3,3,3-hexafluoropropane and one or more unsaturated fluorocarbon compounds, the process comprising:

a) providing a photochlorinator vessel comprising
   1) a UV lamp unit comprising a UV lamp located in a transparent inner well, the transparent inner well being located within a transparent outer well, said outer well being provided with material for cooling walls of the inner and outer wells; the inner well and the outer well defining separate chambers isolated from each other; and
   2) a reaction vessel into which the UV lamp unit has been inserted;
b) introducing into the reaction vessel a gaseous mixture of $Cl_2$ and a distillation inseparable mixture of 1,1,1,3,3,3-hexafluoropropane and one or more unsaturated fluorocarbon compounds;
c) reacting, in the gaseous state and in the presence of UV light from the photochlorinator, the mixture with $Cl_2$ with the distillation inseparable mixture of 1,1,1,3,3,3-hexafluoropropane and one or more unsaturated compounds to saturate unsaturated fluorocarbons into a reacted mixture, and
d) separating a purified 1,1,1,3,3,3-hexafluoropropane product containing less than 1000 ppm, preferably less than 500 ppm, and more preferably less than 100 ppm unsaturated fluorocarbons. In another embodiment, step d) comprises distilling the reacted mixture to obtain the purified 1,1,1,3,3,3-hexafluoropropane product. In a still further embodiment of the invention, the continuous vapor phase method comprises the additional step e) of removing residual HCl and chlorine from the 1,1,1,3,3,3-hexafluoropropane at any point in the method subsequent to reacting the mixture with $Cl_2$ to saturate the unsaturated fluorocarbons. In an even further embodiment of the invention, step e) is performed between steps c) and d) and comprises washing the reacted mixture with an aqueous solution to remove the residual HCl and chlorine and removing the aqueous solution.

The continuous, vapor phase method preferably comprises:

a) providing a photochlorinator vessel comprising:
   1. a UV lamp unit comprising a UV lamp located in a transparent inner well, the transparent inner well being located within a transparent outer well, said outer well being provided with material for cooling the walls of the inner and outer wells; the inner well and the outer well defining separate chambers isolated from each other; and
   2. a reaction vessel into which the UV lamp unit has been inserted;
b) introducing into the reaction vessel a gaseous mixture of $Cl_2$ and a distillation inseparable mixture of 1,1,1,3,3,3-hexafluoropropane and one or more unsaturated fluorocarbon compounds;
c) reacting, in the presence of UV light from the photochlorinator, the mixture with $Cl_2$ with the distillation inseparable mixture of 1,1,1,3,3,3-hexafluoropropane and one or more unsaturated compounds to saturate the unsaturated fluorocarbon(s) into a reacted mixture,
d) washing the reacted mixture with an aqueous solution to remove residual hydrochloric acid and $Cl_2$,
e) removing the aqueous solution,
f) distilling the reacted mixture to from which the aqueous solution has been removed to obtain a purified 1,1,1,3,3,3-hexafluoropropane containing <1000 ppm, preferably <500 ppm, and more preferably <100 ppm unsaturated fluorocarbons.

DETAILED DESCRIPTION OF THE INVENTION

In accordance with the invention a continuous, vapor phase method is provided to purify HFC-236fa from a crude product mixture containing HFC-236fa and other saturated and unsaturated halocarbons including hydrofluorocarbons (HFC's), chlorofluorocarbons (CFC's) and hydrochlorofluorocarbons (HCFC's), any of which may be saturated or ethylenically unsaturated. The crude product can be produced by several different reaction methods as previously described. The invention comprises a continuous, vapor phase method for purifying a crude mixture of 1,1,1,3,3,3-hexafluoropropane and one or more unsaturated fluorocarbon compounds, the process comprising:

a) providing a photochlorinator vessel comprising
   1) a UV lamp unit comprising a UV lamp located in a transparent inner well, the transparent inner well being located within a transparent outer well, said outer well being provided with material for cooling walls of the inner and outer wells; the inner well and the outer well defining separate chambers isolated from each other; and
   2) a reaction vessel into which the UV lamp unit has been inserted;
b) introducing into the reaction vessel a gaseous mixture of $Cl_2$ and a distillation inseparable mixture of 1,1,1,3,3,3-hexafluoropropane and one or more unsaturated fluorocarbon compounds;
c) reacting, in the gaseous state and in the presence of UV light from the photochlorinator, the mixture with $Cl_2$ with the distillation inseparable mixture of 1,1,1,3,3,3-hexafluoropropane and one or more unsaturated compounds to saturate unsaturated fluorocarbons into a reacted mixture, and
d) separating a purified 1,1,1,3,3,3-hexafluoropropane product containing less than 1000 ppm, preferably less than 500 ppm, and more preferably less than 100 ppm unsaturated fluorocarbons. In another embodiment, step d) comprises distilling the reacted mixture to obtain the purified 1,1,1,3,3,3-hexafluoropropane product. In a still further embodiment of the invention, the continuous vapor phase method comprises the additional step e) of removing residual HCl and chlorine from the 1,1,1,3,3,3-hexafluoropropane at any point in the method subsequent to reacting the mixture with $Cl_2$ to saturate the unsaturated fluorocarbons. In an even further embodiment of the invention, step e) is performed between steps c) and d) and comprises washing the reacted mixture with an aqueous solution to remove the residual HCl and chlorine and removing the aqueous solution.

The continuous, vapor phase method preferably comprises:

a) providing a photochlorinator vessel comprising
   1. a UV lamp unit comprising a UV lamp located in a transparent inner well, the transparent inner well being located within a transparent outer well, said outer well being provided with material for cooling the walls of the inner and outer wells; and
   2. a reaction vessel into which the UV lamp unit has been inserted;
b) introducing into the reaction vessel a gaseous mixture of $Cl_2$ and a distillation inseparable mixture of 1,1,1,3,3,3-hexafluoropropane and one or more unsaturated fluorocarbon compounds;

c) reacting, in the presence of UV light from the photochlorinator, the mixture with $Cl_2$ with the distillation inseparable mixture of 1,1,1,3,3,3-hexafluoropropane and one or more unsaturated compounds to saturate the unsaturated fluorocarbon(s) into a reacted mixture, d) washing the reacted mixture with an aqueous solution to remove residual hydrochloric acid and $Cl_2$, e) removing the aqueous solution, f) distilling the reacted mixture to from which the aqueous solution has been removed to obtain a purified 1,1,1,3,3,3-hexafluoropropane product containing <1000 ppm, preferably <500 ppm, and more preferably <100 ppm unsaturated fluorocarbons.

Fluorocarbon" as used herein means a carbon chain to which one or more fluorine atoms are attached. The carbon chain may be perfluorinated, i.e., saturated with fluorine, or may only be partially fluorinated. Partially fluorinated carbon chains may be ethylenically unsaturated, i.e. contain alkene structures, and may have attached hydrogen, chlorine, or bromine atoms. The generic term "fluorocarbon" thus includes HFC's, HCFC's and CFC's.

The crude 1,1,1,3,3,3-hexafluoropropane from initial liquid phase synthesis typically contains from about 20 to 40 weight percent fluorocarbon impurities, e.g., 1,1,1,3,3-pentafluoropropene (HFC1225zc); 1,1,1,3,3-pentafluoro-2-chloropropene (HCFC1215xc); 1,1,1,3-tetrafluoro-3-chloropropene (HCFC1224zc); 1,1-difluoro-2,2-dichloroethene HCFC1112a); trichlorofluoromethane (CFC11) and 1,1, 1,3,3-pentafluoro-3-chloropropane HCFC235fa).

The crude 1,1,1,3,3,3-hexafluoropropane obtained by liquid phase reaction is distilled to remove most impurities. The result is an azeotropic mixture of 1,1,1,3,3-pentafluoropropane and 1,1,1,3,3,3-hexafluoro-2-chloropropene with less than about 0.5 percent by weight of other fluorocarbons.

"Close boiling mixture" as used herein means a mixture of compounds which boil so close together that they vaporize at about the same temperature. Examples of such close boiling mixtures are described in U.S. Pat. No. 5,414,165 and comprise about 99 weight percent 1,1,1,3,3,3-hexafluoropropane, about 0.2 to about 0.7 weight percent of the unsaturated isomer of $C_3HCl_2F_3$, the balance being other fluorocarbons.

"Azeotropic mixture" as used herein means a mixture of compounds which together boil (vaporize) at a temperature lower than the boiling temperature of any of the compounds independently. The azeotrope separated by distillation from preparation by liquid phase reaction, in accordance with the present invention, may comprise about 95 weight percent or more of 1,1,1,3,3,3-hexafluoropropane and about 5 weight percent or less of fluorocarbon impurities. The most prevalent fluorocarbon impurity in the azeotrope is usually 1,1,1,3,3-pentafluoro-2-chloropropene. For example, a specific azeotropic mixture obtained by distillation from liquid phase reaction was found to contain between about 97 and about 98 weight percent 1,1,1,3,3,3 hexafluoropropane, about 0.007 weight percent 1,1,1,3,3-pentafluoropropene; between about 2 and about 3 weight percent of 1,1,1,3,3-pentafluoro-2-chloropropene; about 0.08 weight percent 1,1,-difluoro-2,2-dichloroethene; and about 0.05 weight percent of trichlorofluoromethane.

"Reacting the mixture with chlorine" means that unsaturated compounds in the distillation inseparable mixture are reacted with chlorine in the presence of UV light so that chlorine is added across double bonds of the unsaturated compounds to chlorine saturate the double bonds.

The reacting of said mixture with chlorine occurs in the vapor phase at about a pressure of from about 0 psig to about 50 psig, preferably from about 1 psig to about 15 psig, more preferably from about 2 psig to about 10 psig, and most preferably at about 5 psig. The temperature of the reaction is generally at from about –1° C. to about 100° C., preferably from about 5° C. to about 70° C., more preferably from about 15° C. to about 50° C., and most preferably at ambient temperature.

Saturating the unsaturated fluorocarbons with chlorine changes their boiling points. Therefore, after reacting with chlorine, the mixture is treated by conventional techniques, such as by distillation, to remove remaining fluorocarbons impurities.

Desirably, subsequent to reaction with chlorine and prior to the next purification step, e.g., distillation, residual hydrochloric acid and chlorine are usually removed even though the distillation step itself may separate the 1,1,1,3,3,3-hexafluoropropane from HCl and chlorine. This is because the removal of HCl and chlorine in the distillation step is usually not complete. Residual hydrochloric acid and chlorine, either prior to or subsequent to distillation, are usually removed by washing with an aqueous solution and then removing the aqueous solution.

"Hydrochloric acid" as used herein is intended to include hydrogen chloride (HCl), whether or not it is dissolved in water.

After chlorination, the reacted mixture is usually washed by an aqueous solution, containing acid neutralizing agents and chlorine reactants, e.g., caustic and a bisulfite, to neutralize excess chlorine and hydrochloric acid. The resulting aqueous solution is then separated from the resulting fluorocarbon. In the case of liquid washing a major portion of the aqueous phase is usually separated by allowing the mixture of the aqueous phase and fluorocarbon phase to phase separate into an upper aqueous phase and a lower fluorocarbon phase and drawing the lower fluorocarbon phase from beneath the aqueous phase. "Caustic" means an aqueous solution comprising sodium hydroxide, potassium hydroxide or mixtures thereof. The amount of sodium or potassium hydroxide in the aqueous solution is usually from about 0.01 to about 0.5 weight percent. "Bisulfite" means any water soluble bisulfite, especially sodium and potassium bisulfites. The amount of bisulfite in the aqueous solution is usually from about 0.01 to about 0.02 weight percent. Other acid neutralizing agents such as alkaline earth hydroxides, e.g. calcium or magnesium hydroxides, can be used.

After separation of the fluorocarbon from the aqueous washing solution, it is usually dried to remove residual water prior to distilling. Drying can be done by any suitable drying method, such as for example, with sulfuric acid or a desiccant. "Desiccant" means any material which will absorb water without dissolving in or otherwise contaminating the fluorocarbon being dried, e.g., calcium sulfate or molecular sieves.

Chlorine can also be removed by reactive organics, such as for example, methyl styrene. When such a reactive organic us used, it may react with residual chlorine subsequent to the chlorine unsaturated fluorocarbon reaction and prior to washing with aqueous solution. The chlorine—chlorine reactive organic compound product may then be removed in the next distillation step.

The UV light source utilized in the UV unit is sized such as to provide UV output of from about 0.01 to about 10.0 watts-hours/kg of the reaction mixture, preferably from about 0.02 to about 2.0 watts-hours/kg of the reaction mixture, most preferably from about 0.1 to about 1.0 watts-hours/kg of the reaction mixture. The UV light is one having a wavelength of from about 300 to about 400 nm. The ultraviolet light source may be any suitable such light source and may be provided by arc lamps such as, for example, mercury, argon or xenon arc lamps, and filament lamps such as, for example, tungsten and halogen filament lamps. The actual useful UV output watts of each lamp is dependent on the characteristics of the lamp selected. For example, a 10 KW UV lamp typically outputs 1.2 KW (or 12%) of UV light at the 300 to 400 nm wavelength range.

The invention may be further illustrated by reference to the drawings of one exemplary, but non-limiting embodiment of the invention. A general overview of the method or process is illustrated in FIG. 1. Stream 1 is fed into distillation column 11. Stream 1 contains crude 1,1,1,3,3,3-hexafluoropropane, such as that prepared by liquid phase methods known to those skilled in the art as described in U.S. Pat. No. 5,395,997, previously discussed. Stream 2, exiting the top of column 11 can be an azeotropic mixture of about 97.6 weight percent 1,1,1,3,3,3-hexafluoropropane and about 2.4 weight percent of 1,1,1,3,3-pentafluoro-2-chloropropene.

Figure 2:
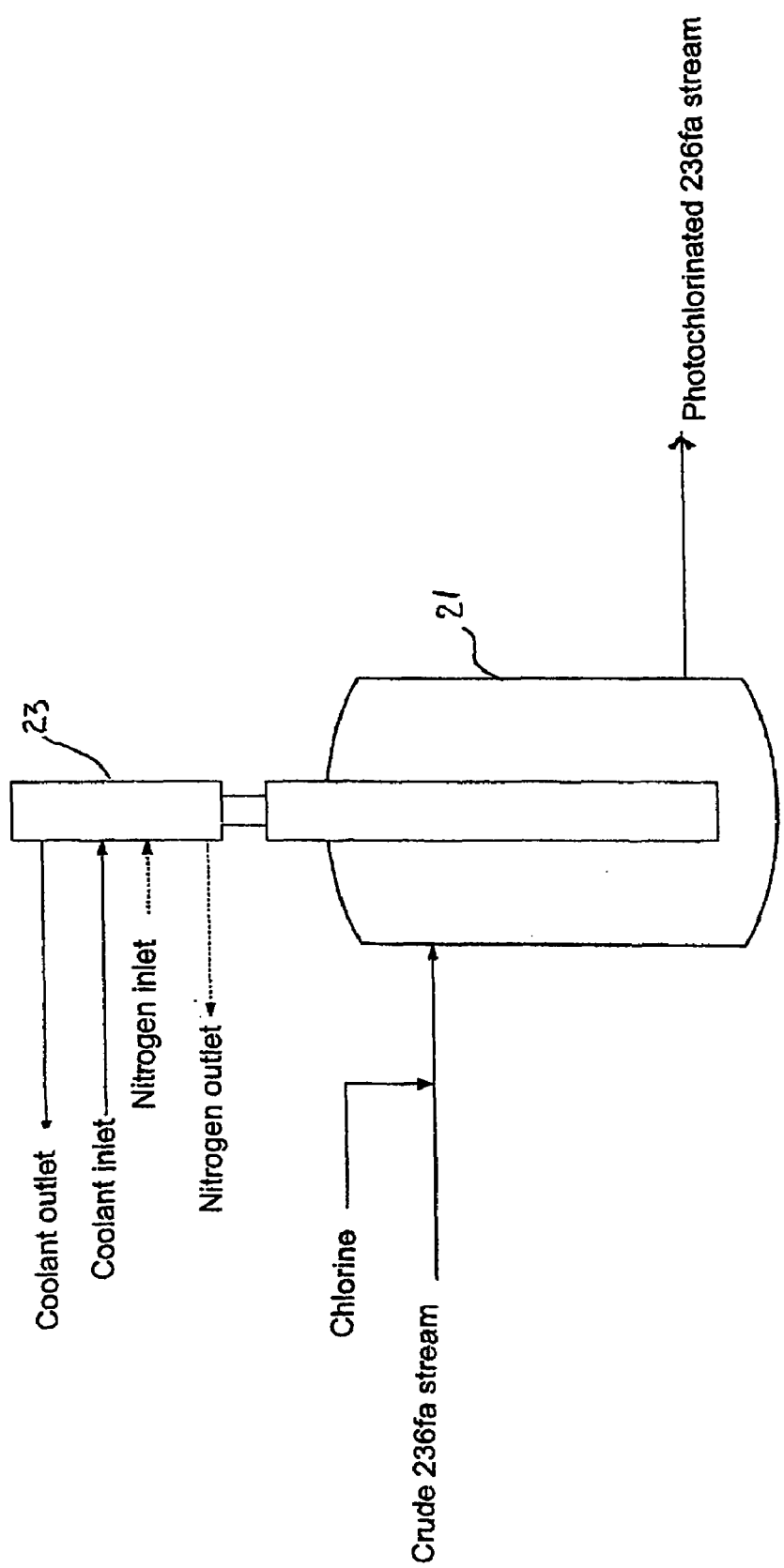
FIG. 2 is a is a elevational schematic view of a photochlorination apparatus used in the method of this invention.

Stream 2 enters photochlorination reactor 21, where a 450 watt UV light source is present and turned on. Stream 3, which is $Cl_2$, may be a separate stream, but is preferably a stream combined with stream 2 prior to entering reactor vessel 21 (as illustrated in FIG. 2). The UV light causes the $Cl_2$ to add across the double bonds of unsaturated impurities, especially 1,1,1,3,3-pentafluoro-2-chloropropene. Reactor 21 is run at about 5 psig, and at ambient temperature. Stream 5, a slightly caustic solution containing the amount of bisulfite required to neutralize unreacted chlorine in reactor 21, is added to scrubber tank 31. Reacted stream 4 exits reactor 21 and is fed and mixed with the caustic bisulfite solution in scrubber tank 31 to neutralize the excess $Cl_2$ or hydrochloric acid with the bisulfite and caustic, respectively. It will be appreciated that reacted stream 4 can be further processed in the gas phase or can be cooled to a liquid stream for subsequent processing steps.

After neutralizing, the halocarbon (stream 6) is separated from the aqueous solution (stream 7). In the case of liquid phase scrubbing, the contents of scrubber tank 31 is allowed to phase separate into an upper aqueous phase and a lower halocarbon phase. The halocarbon phase is then removed from the bottom of mixing tank 31 as stream 6. After removal of stream 6, the aqueous phase is removed as stream 7.

Dried stream 8 from drying column 41 enters distillation column 51 for separation of 1,1,1,3,3,3-hexafluoropropane from impurities. Steam 9 taken from the column 51 is greater than 99.9 weight percent 1,1,1,3,3,3-hexafluoropropane containing less than 100 ppm of unsaturated fluorocarbons. Stream 10 comprised removed impurities.

Figure 3:
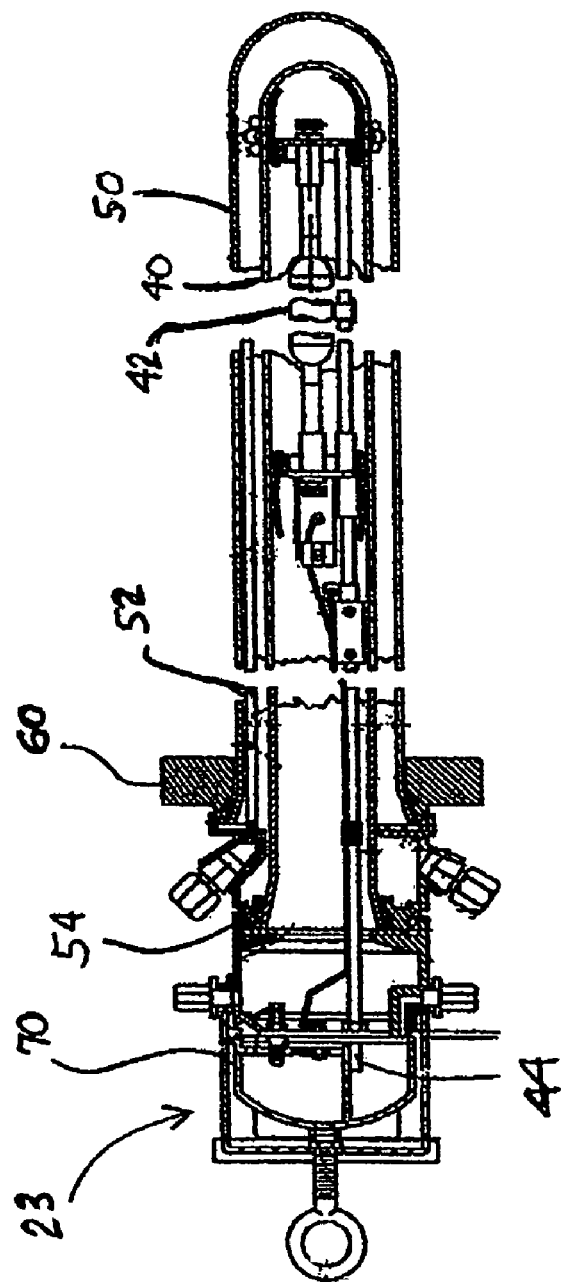
FIG. 3 is a view, partially in section, of a UV Unit of the UV photochlorination apparatus of this invention

The photochlorinator vessel, combined elements UV unit 23 and reaction vessel 21, is generally illustrated in FIG. 2 which is not to scale. An exemplary UV unit 23 is illustrated in FIG. 3. Referring to FIG. 3 the UV unit 23 comprises an inner well 40 and a surrounding outer well 50. The two well define distinct chambers isolated from each other, such as for example by way of a sealant ring 54. In inner well 40 is located a UV lamp 42 connected to an electrical cap 70 to which an electrical power source (not shown) has been connected to provide power to the UV lamp. An inert, coolant gas, e.g., nitrogen, supply/exhaust line 44 is provided in well 40 to provide gas for keeping the UV lamp 42 from overheating during the reaction and to prevent filament damage. Outer well 50, surrounding inner well 40, has provided therein a coolant supply/exhaust line for providing coolant for cooling the surfaces of the inner and outer wells, particularly the outer well 50 during operation off the reaction. Failure to keep the well walls cool during the reaction can result in undesirable deposit being formed on the outer surface of outer well with the result that UV light is inhibited or prevented from being able to cause the reaction of chlorine gas with the distillation inseparable mixture. Additionally, excess heat from the outer well can cause undesirable decomposition of HFC-236fa. As a coolant water may be use, preferably deionized water. Deionized water will increases the time between required removal of the UV lamp wells 40 and 50 for cleaning because of mineral deposits. The UV unit 23 may be provided with any suitable mounting element for mounting it in reactor 21. For example, UV unit 23 may be provided with a mounting flange 60.

The transparent well of UV unit 23 may be made of any suitable transparent material, but are preferably made of quartz. The reaction vessel 21 is made of any suitable material and is generally carbon steel lined with polytetrafluoroethylene.

As illustrated in FIG. 2 gaseous distillation inseparable HFC-236fa mixture and $Cl_2$ are fed into the reactor vessel 21, such as through a common nozzle. The reacted mixture exits an exit nozzle as photochlorinated HFC-236a stream.

The reaction vessel may be of any suitable size. A useful size is one 16 inch diameter and 9 feet long. A 4 inch nozzle for feed of the gaseous distillation inseparable HFC-236fa mixture and $Cl_2$ and for exit of the photochlorinated product may be employed. Typically these two nozzles are separated by a linear distance of about 8 feet. The reaction vessel may have internal gas distributors and may or may not have baffles, as considered necessary to channel the reaction gas flow and support the lamp unit. Such a UV photochlorination vessel, equipped with a 10 KW UV lamp, may be employed to photochlorinate about 1500 kg/hr of crude HFC-236fa and produce purified HFC-236fa containing less than 1000 ppm, preferably less than 500 ppm, and more preferably less than 100 ppm unsaturated fluorocarbons. One can experimentally determine the optimum watt-hr/kg of the crude feed for any given crude feed rate for any given sized reaction vessel. For example, for 300 kg/hr crude feed rate a 5 KW UV light may be used in a reactor that is about 9 feet long and about 11 inches id.

In another aspect of this invention, two or more UV photochlorination vessels may be used in series for the photochlorination reaction of chlorine with the crude HFC-236fa in order to convert difficult unsaturated fluorocarbons and to minimize chlorine usage, or to obtain a near non-detectable level of unsaturates. In a still further aspect of this invention, the UV photochlorination vessel may be used to process a larger quantity of crude HFC-236fa to reduce a substantial amount of unsaturates, such as a 90% reduction of incoming unsaturates. It is then followed by a polishing step of a second photochlorination vessel or molecular sieve to further reduce the unsaturates level. Additionally, the UV photochlorination vessel of this invention may be utilized to reduce unsaturated fluorocarbons from crude HFC-134a and HFC-245fa.

While the invention has been described herein with reference to the specific embodiments thereof, it will be appreciated that changes, modification and variations can be made without departing from the spirit and scope of the inventive concept disclosed herein. Accordingly, it is intended to embrace all such changes, modification and variations that fall with the spirit and scope of the appended claims.

What is claimed is:

1. A continuous, vapor phase method for purifying a crude mixture comprising 1,1,1,3,3,3-hexafluoropropane and one or more unsaturated fluorocarbon compounds, the process comprising:
    a) providing a photochlorinator vessel comprising
        1) a UV lamp unit comprising a UV lamp located in a transparent inner well, the transparent inner well being located within a transparent outer well, said outer well being provided with material for cooling walls of the inner and outer wells; the inner well and the outer well defining separate chambers isolated from each other; and
        2) a reaction vessel into which the UV lamp unit has been inserted;
    b) introducing into the reaction vessel a gaseous $Cl_2$ and a mixture comprising 1,1,1,3,3,3-hexafluoropropane and one or more unsaturated fluorocarbon compounds;
    c) reacting, in the gaseous state and in the presence of UV light from the photochlorinator, the $Cl_2$ with the mixture to produce a reacted mixture, and
    d) separating a purified 1,1,1,3,3,3-hexafluoropropane product containing less than 1000 ppm unsaturated fluorocarbons.

2. The method of claim 1, wherein step d) comprises distilling the reacted mixture to obtain the purified 1,1,1,3,3-hexafluoropropane product.

3. The method of claim 1, additionally comprising the step e) of removing residual HCl and chlorine from the 1,1,1,3,3,3-hexafluoropropane at any point in the method subsequent to reacting the mixture with $Cl_2$.

4. The method of claim 2, additionally comprising the step e) of removing residual HCl and chlorine from the 1,1,1,3,3,3-hexafluoropropane at any point in the method subsequent to reacting the mixture with $Cl_2$.

5. The continuous vapor phase method of claim 3, wherein step e) is performed between steps c) and d) and comprises washing the reacted mixture with an aqueous solution to remove the residual HCl and chlorine and removing the aqueous solution.

6. The method of claim 4, wherein step e) is performed between steps c) and d) and comprises washing the reacted mixture with an aqueous solution to remove the residual HCl and chlorine and removing the aqueous solution.

7. The method of claim 1, wherein the purified 1,1,1,3,3,3-hexafluoropropane product is one containing <100 ppm unsaturated fluorocarbons.

8. The method of claim 1, wherein the inner well is provided with an inlet for an inert material for cooling.

9. The method of claim 8, wherein the material for cooling provided in the outer well is deionized water and the inert material for cooling provided in the inner well is nitrogen.

10. The method of claim 1, wherein the transparent inner and outer wells are quartz wells.

11. The continuous, vapor phase method of claim 1, wherein the UV lamp provides UV light of a wavelength of from about 300 to about 400 nm.

12. The method of claim 1, wherein the purified 1,1,1,3,3,3-hexafluoropropane is of about 99.9% purity.

13. The method of claim 1, wherein at least two photochlorination vessel units are provided in series.

14. The continuous, vapor phase method of claim 1, wherein the reaction in the photochlorination vessel unit reduces a substantial amount of unsaturated fluorocarbon compound(s), and the reaction is followed by a subsequent polishing step to further reduce the amount of unsaturated fluorocarbon compound(s).

15. The method of claim 1, wherein the gaseous $CL_2$ and the mixture comprising 1,1,1,3,3,3-hexafluoropropane and one or more unsaturated fluorocarbon compounds are combined before their introduction into the reaction vessel.

16. The method of claim 1, wherein the photochlorination reaction is conducted at ambient temperature and at a pressure of about 5 psig.

17. The method of claim 1, wherein the mixture comprising 1,1,1,3,3,3-hexafluoropropane and one or more unsaturated fluorocarbon compounds of step b) comprises a distillation inseperable mixture.

18. The method of claim 3, wherein the mixture comprising 1,1,1,3,3,3-hexafluoropropane and one or more unsaturated fluorocarbon compounds of step b) comprises a distillation inseparable mixture.

19. The method of claim 7, wherein the mixture comprising 1,1,1,3,3,3-hexafluoropropane and one or more unsaturated fluorocarbon compounds of step b) comprises a distillation inseparable mixture.

20. The method of claim 15, wherein the mixture comprising 1,1,1,3,3,3-hexafluoropropane and one or more unsaturated fluorocarbon compounds of step b) comprises a distillation inseparable mixture.

* * * * *